United States Patent [19]
Maresch et al.

[11] Patent Number: 6,099,461
[45] Date of Patent: Aug. 8, 2000

[54] DEVICE FOR HUMIDIFYING THE USEFUL SPACE OF A CLIMATIC TEST CABINET

[75] Inventors: Lothar Maresch, Mömbris; Egon Hessler, Hasselroth, both of Germany

[73] Assignee: Kendro Laboratory Products GmbH, Hanau, Germany

[21] Appl. No.: 09/179,661

[22] Filed: Oct. 27, 1998

[30] Foreign Application Priority Data

Oct. 28, 1997 [DE] Germany .................. 197 47 498

[51] Int. Cl.[7] .................................................. A61G 11/00
[52] U.S. Cl. ............................................................ 600/22
[58] Field of Search ........................................ 600/21–22

[56] References Cited

U.S. PATENT DOCUMENTS

| | | | |
|---|---|---|---|
| 4,923,816 | 5/1990 | Heeg et al. | 425/284 |
| 5,242,375 | 9/1993 | McDonough | 600/22 |

FOREIGN PATENT DOCUMENTS

| | | |
|---|---|---|
| 1 027 368 | 10/1956 | Germany . |
| 7633120 | 2/1977 | Germany . |
| 38 15 528 | 8/1989 | Germany . |

OTHER PUBLICATIONS

Abstract of Japanese Patent Publication No. 06347107, published Dec. 20, 1994.

*Primary Examiner*—John P. Lacyk
*Attorney, Agent, or Firm*—Workman, Nydegger & Seeley

[57] ABSTRACT

A climatic cabinet such as a climatic test cabinet or gassing incubator includes a housing bounding a useful space. The useful space communicates with the exterior through a front opening. The housing includes a floor having a back wall and opposing sidewalls upstanding therefrom. The floor is inclined at least at the front opening so as to slope down from the front opening towards the back wall. The floor bounds a trough configured to retain water remote from the front opening.

18 Claims, 2 Drawing Sheets

DEVICE FOR HUMIDIFYING THE USEFUL SPACE OF A CLIMATIC TEST CABINET

The present application claims priority under 35 U.S.C. § 119 to German Patent Application No. 197 47 498.5, filed Oct. 28, 1997, which is incorporated herein by specific reference.

BACKGROUND OF THE INVENTION

1. The Field of the Invention

The invention concerns a device for humidifying the useful space of a climatic test cabinet, especially a gassing incubator.

2. Present State of the Art

Various types of humidifying devices are used to humidify the air in the useful space of climatic test cabinets or gassing incubators. According to one type, water from a water supply outside the useful space is vaporized and the aerosol is fed into the useful space. Another way of humidifying the air in the useful space is by arranging a water container directly in the useful space and evaporating the water therein. Normally for this purpose a separately removable water trough is arranged on the floor of the useful space and heated with a suitable heating device. The heating element can be arranged directly in the water bath or in the immediate vicinity of the water bath. Alternatively, the useful space is equipped with a trough-shaped bottom area.

For example, a humidifying or steam sterilization device according to the last-mentioned principle is known from DE-AS 10 27 368. This patent describes a sterilization cabinet having a useful space with a floor area in the form of a trough which is filled with water to be evaporated. The water is connected with an external water supply container via a feed and drain system. Toward the door of the sterilization cabinet, the trough is bordered by a wall-like vertical plate.

A gassing incubator is also known from DE 38 15 528 which is also equipped with a water-filled trough on the floor of the useful space or with a floor area of the useful space in the form of a trough, which is intended to humidify the useful space. If an inserted rectangular trough is used, then it lies flat on the floor of the useful space and is bordered on all four sides by vertical side walls which prevent the water flowing out.

In the case when the floor of the useful space is shaped like a trough, a cross-strip is arranged in the lower part of the opening of the gassing incubator's useful space. This design makes it quite difficult to clean the water container in the floor area of the useful space, especially in the front area pointing toward the opening of the useful space. This is because the front cross-strip makes the area lying directly behind it only poorly accessible for inspection and for introducing cleaning materials, such as, for example cleaning cloths.

When a separate removable trough is used with a level floor and vertical side walls all around it, there is the further disadvantage that condensation forms outside the trough. Precisely in the front area of the useful space near the opening, the water bath which projects into this area encourages the humidity of the outside air entering at the opening of the useful space to condense outside on the side walls of the trough. The so-called humidity recovery time, which is the time required after the gassing incubator is opened until the humidity values have restabilized, is also substantially longer for a humidifying device with a removable trough. This is because such designs provide relatively poor heat transfer from the heating device to the water bath compared to a useful space with a built-in trough-shaped floor area.

OBJECTS AND BRIEF SUMMARY OF THE INVENTION

Starting from the existing state of the art which has been presented, the present invention is based on the task of specifying a device for humidifying the useful space of a climatic test cabinet, especially a gassing incubator, which allows optimal cleaning of the water container to reduce the danger of contamination, which excludes, or at least reduces, the danger of condensation outside the water container, and which can be produced economically.

This task is solved by giving the useful space an inclined floor surface, at least in the area of the opening of the useful space. The higher area of the floor surface is oriented toward the opening of the useful space, without being bordered by a side wall. The lower area of the floor surface is oriented toward the back of the useful space or connecting directly with the back.

This design allows the humidifying device to be easily cleaned from the opening of the useful space. The cleaning material can be introduced on the inclined floor surface which drops toward the back in the useful space of the climatic test cabinet or gassing incubator. Doing away with a front vertical side wall or cross-strip makes possible the immediate recognition and easy removal of contaminants even on the front part of the humidifying device according to the invention. The depth of the water bath increases in the direction toward the back wall of the useful space due to the inclination of the floor of the useful space. Therefore, the front area of the humidifying device oriented toward the opening of the useful space will have no water at all or only a few millimeters of water standing in it, depending on how full it is.

The coldest area of the useful space for the formation of condensation is about 10 cm above the water bath on the back wall of the useful space. The condensed water, for example from the outside air entering when the useful space is opened, preferentially condenses at the coldest area and immediately flows from there into the water bath.

The invention also provides a cost advantage to the manufacturer of climatic test cabinets and gassing incubators by eliminating the otherwise commonly used front perpendicular side wall or cross-strip in the lower area of the opening of the useful space.

It is expedient for the inclined floor surface of the useful space of a climatic test cabinet or gassing incubator to have an incline of 2° to 10°.

To give an approximate indication of the amount of water in the humidifying device, the inclined floor surface of the useful space has markings in its higher area. For example, the markings can be chiseled or stamped in the floor surface or they can be small, knob-like elevations or bulges on the floor surface or on one of several of the three side walls.

The following description of the embodiment of the invention uses the drawings to provide more details and features of the invention.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
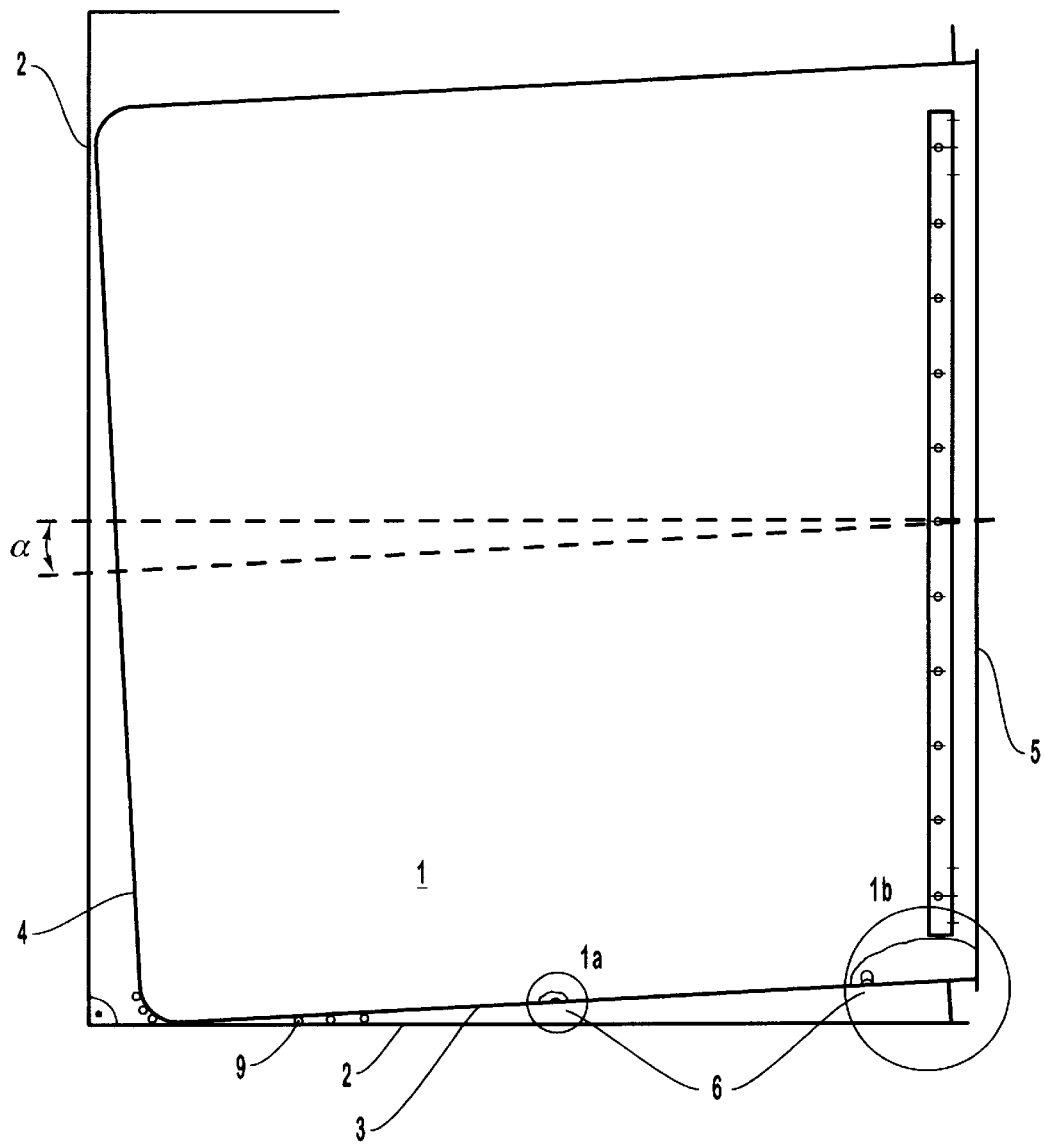
FIG. 1 shows a side view of the useful space of a gassing incubator having an inclined floor surface.

FIG. 1 shows a simple embodiment of the humidifying device according to the present invention. It shows in side view how the useful space or inside housing, in a known embodiment, is inserted at an incline in the outside housing 2 of an incubator, which is used, for example, in medical or biological research. Here the lower area of the useful space 1 serves as a trough with an inclined floor surface 3 to hold water, the inclination being in the direction of the back wall 4 of the useful space 1 or the incubator. In this case the angle of inclination α is 3°. In one example, the inside dimensions of the useful space 1 are 470 mm (width), 530 mm (depth), and 607 (height). As a result, the maximum amount of water useful space 1 can be filled with is 3 liters. The heating elements 9 needed to promote water evaporation are arranged below the floor surface 3 and in the lower area, outside the useful space 1.

The inclined floor surface 3 in the front area oriented toward the opening 5 of the useful space 1 is not bordered by a vertical side wall or cross-strip, so that it is freely accessible and visible from opening 5 of useful space 1. In this way no "dead angle" remains for cleaning.

The condensation of water outside this humidifying device is also practically impossible. Water which might come from the outside air (when the useful space is opened) is condensed only on the water bath itself or on the back wall 4 of the useful space 1 a short distance above the water bath, and not, for instance, outside on a cross-strip.

In order to give the operators a rough idea about the amount of water to fill into useful space 1, the inclined floor surface 3 has markings 6 in the form of a bulge-like impression 6' (about 3 to 5 mm in height). These bulge-like impression 6' are positioned roughly in the middle and near the opening 5 of the useful space 1. The bulge-like impression 6' can be made over the entire useful space or width of the wall.

Figure 1A:
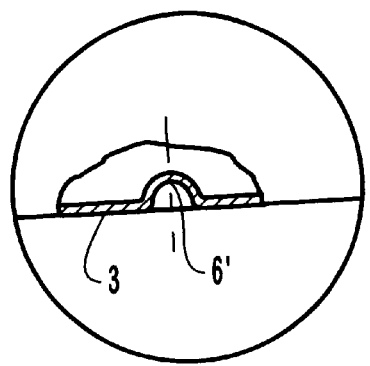
FIGS. 1a and 1b show the enlarged sections from FIG. 1 with bulge-like impressions on the floor surface.
Figure 1B:
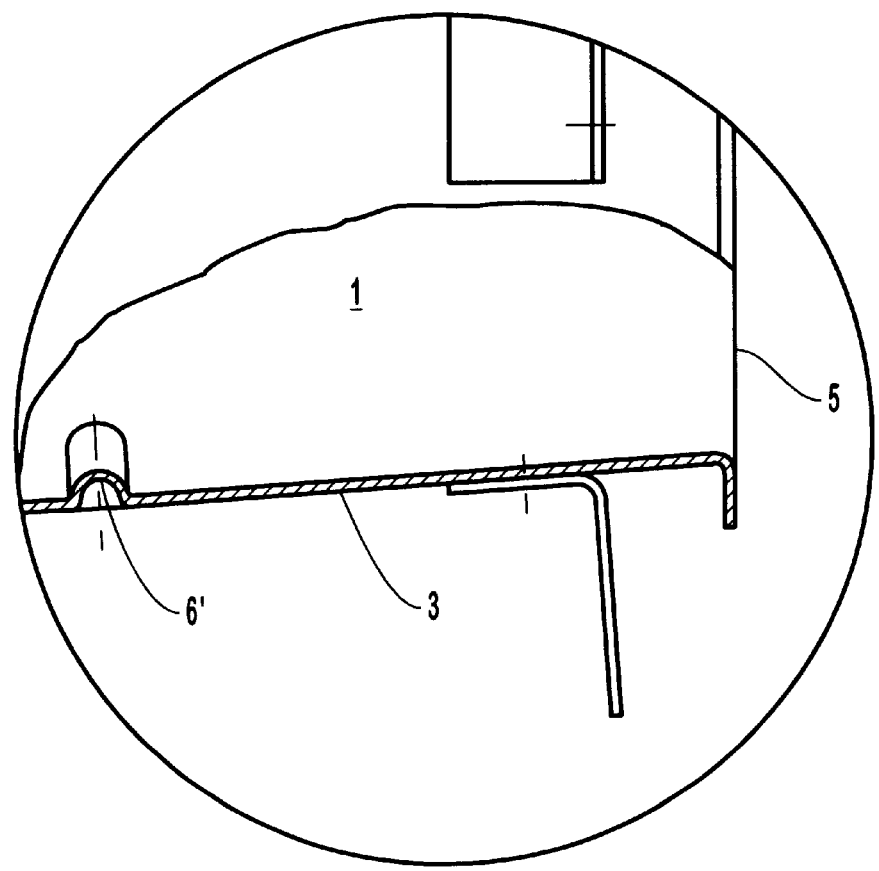

FIGS. 1a and 1b show these stamps 6' as enlargements corresponding to the original size.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A component of a climatic cabinet comprising a housing bounding a useful space and having a front opening, the housing including a floor having a back wall and opposing sidewalls upstanding therefrom, the floor being inclined at least at the front opening to slope down from the front opening and forming a trough configured to retain water remote from the front opening, markings being formed on the floor to determine how much water is in the trough.

2. A component of a climatic cabinet as recited in claim 1, wherein the floor is inclined at an angle in a range between about 2° to about 10° relative to the horizontal.

3. A component of a climatic cabinet as recited in claim 1, wherein the trough is formed adjacent to the back wall.

4. A component of a climatic cabinet as recited in claim 1, wherein the housing comprises:

an outside housing bounding a compartment; and an inside housing disposed within the compartment of the outside housing; the inside housing bounding the useful space.

5. A component of a climatic cabinet as recited in claim 1, wherein the floor is substantially flat and is inclined at a substantially constant angle from the opening to the back wall.

6. A climatic cabinet comprising:

a housing as recited in claim 1, and a heating element positioned adjacent to the trough.

7. A component of a climatic cabinet comprising a housing bounding a useful space and having a front opening, the housing including a floor having a back wall and opposing sidewalls upstanding therefrom, the floor being inclined to slope down from the opening to the back wall so that a trough configured to retain water is formed adjacent to the back wall, markings being formed on the floor to determine how much water is in the trough.

8. A component of a climatic cabinet as recited in claim 7, wherein the floor is inclined at an angle in a range between about 2° to about 10° relative to the horizontal.

9. A component of a climatic cabinet as recited in claim 7, wherein the housing comprises:

an outside housing bounding a compartment; and an inside housing bounding the useful space and being disposed within the compartment of the outside housing, the inside housing having the floor with the back wall and opposing sidewalls upstanding therefrom.

10. A component of a climatic cabinet as recited in claim 7, wherein the floor is inclined at a substantially constant angle from the opening to the back wall.

11. A climatic cabinet comprising:

a housing as recited in claim 1, and a heating element positioned adjacent to the trough.

12. A component of a climatic cabinet as recited in claim 7, wherein the floor, back wall, and opposing side walls are formed as an integral unit.

13. A component of a climatic cabinet as recited in claim 7, wherein the floor has a substantially flat top surface adjacent to the opening.

14. A climatic cabinet comprising:

(a) an outside housing having a substantially flat floor and bounding a compartment, the compartment communicating with the exterior through a front opening;

(b) an inside housing disposed within the compartment of the outside housing, the inside housing having a front opening aligned with the front opening of the outside housing and communicating with the exterior, the housing including a floor, having a back wall and opposing sidewalls upstanding therefrom, the floor being inclined to slope down from the opening toward the back wall so that a trough configured to retain water is formed adjacent to the back wall; and (c) a heating element positioned between the outer housing and the inner housing below the trough.

15. A climatic cabinet as recited in claim 14, wherein the floor of the inside housing is inclined at an angle in a range between about 2° to about 10° relative to the floor of the outside housing.

16. A climatic cabinet as recited in claim 14, further comprising markings being formed on the floor of the inside housing to determine how much water is in the trough.

17. A climatic cabinet as recited in claim 14, wherein the floor of the inside housing is inclined at a substantially constant angle from the opening to the back wall.

18. A climatic cabinet as recited in claim 14, wherein the floor, back wall, and opposing side walls of the inside housing are formed as an integral unit.

* * * * *

UNITED STATES PATENT AND TRADEMARK OFFICE
CERTIFICATE OF CORRECTION

PATENT NO. : 6,099,461
DATED : August 8, 2000
INVENTOR(S) : Lothar Maresch; Egon Hessler Page 1 of 1

It is certified that error appears in the above-identified patent and that said Letters Patent is hereby corrected as shown below:

<u>Column 3,</u>
Line 27, before "(height)" change "607" to -- 607 mm --

Signed and Sealed this

Thirtieth Day of October, 2001

Attest:

*Attesting Officer*

NICHOLAS P. GODICI
*Acting Director of the United States Patent and Trademark Office*